United States Patent [19]

Itsuzaki et al.

[11] Patent Number: 5,763,265
[45] Date of Patent: Jun. 9, 1998

[54] SPECIMEN TESTING METHOD AND APPARATUS

[75] Inventors: Yoshihiro Itsuzaki, Kashihara; Yoshikazu Okahashi, Ikoma; Yoshiro Hanashima, Matsudo, all of Japan

[73] Assignee: Matsushita Electric Industrial Co., Ltd., Japan

[21] Appl. No.: 676,520

[22] Filed: Jul. 2, 1996

[30] Foreign Application Priority Data

Jul. 7, 1995 [JP] Japan ................... 7-171845

[51] Int. Cl.$^6$ ..................... C12M 1/34
[52] U.S. Cl. ............... 435/288.7; 422/82.09
[58] Field of Search ................. 210/740, 745, 210/744, 782, 104, 143, 85, 91, 94, 142, 789; 422/72, 102, 82; 436/43, 45, 63, 150

[56] References Cited

U.S. PATENT DOCUMENTS 4,927,545  5/1990  Roginski .................. 210/745
5,308,506  5/1994  McEwen et al. ............ 210/745

Primary Examiner—James Ketter
Assistant Examiner—Irem Yucel
Attorney, Agent, or Firm—Parkhurst & Wendel

[57] ABSTRACT

A specimen testing method and an apparatus capable of extracting accurate serum components depending on a patient even if the amount of the serum components in blood varies in each specimen. The apparatus comprises a visual sensor for taking an image of blood separated into serum components and clot components, an image memory for storing digital image data output from the visual sensor, a serum component upper boundary position detecting means for detecting an upper boundary position of the serum components from the digital image data stored in the image memory, a serum component lower boundary position detecting means for detecting a lower boundary position of the serum components, and a serum component amount measuring means for measuring the amount of the serum components from the upper boundary position and lower boundary position.

6 Claims, 7 Drawing Sheets

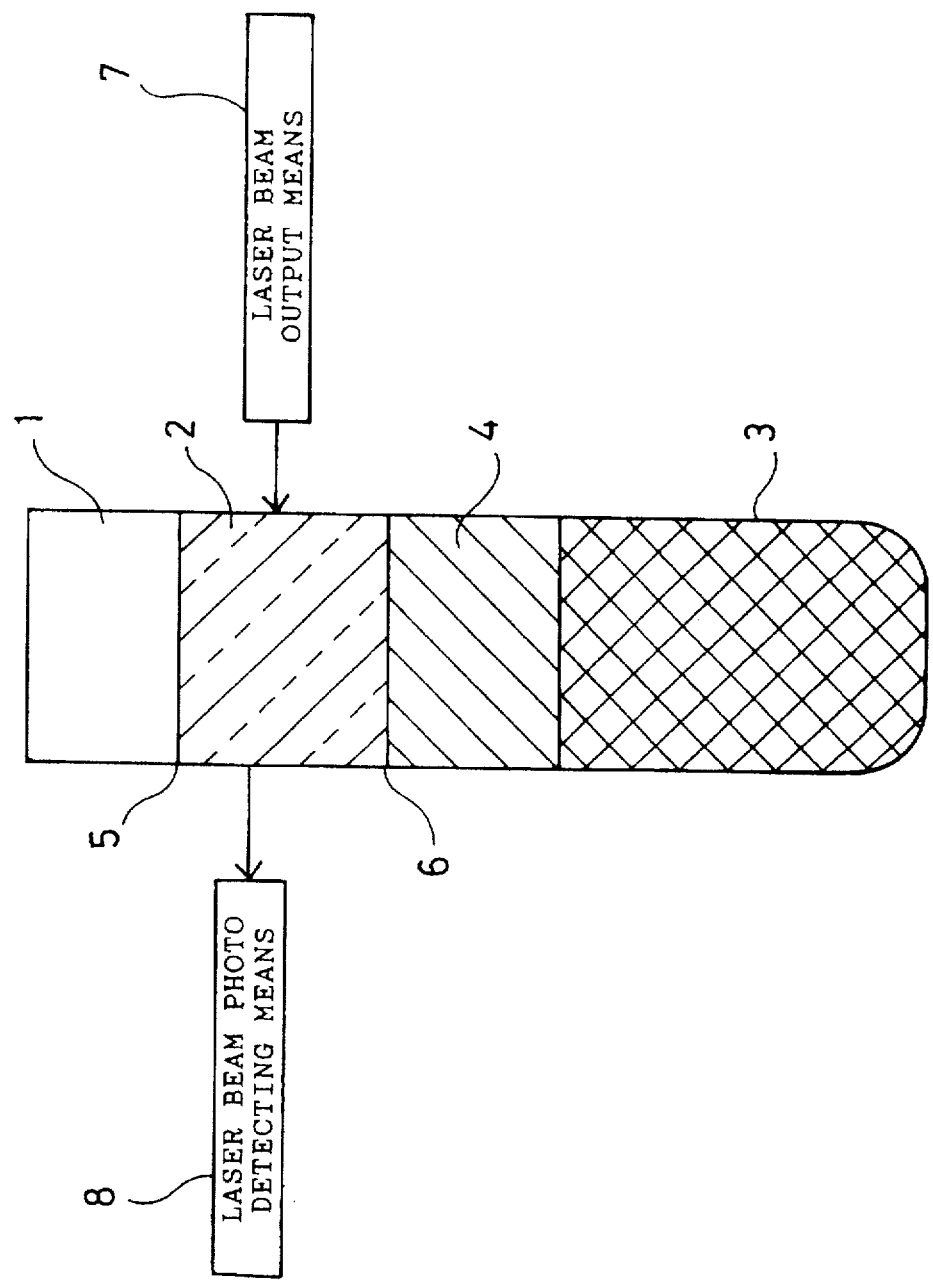

SPECIMEN TESTING METHOD AND APPARATUS

FIELD OF THE INVENTION

The present invention relates to a specimen testing method and its apparatus for extracting only serum components from blood sampled from a patient at hospital or the like, and examining pathological conditions of the patient.

BACKGROUND OF THE INVENTION

To diagnose diseases of patients, an apparatus for analyzing blood sampled from patients has been used widely in many hospitals.

As a conventional example of specimen testing methods, a blood testing method is described below. FIG. 8 is a diagram for describing a conventional blood testing method, in which numeral 1 denotes separated blood of blood sampled from a patient and separated into serum components 2 and clot components 3 by centrifuge or the like, and 4 is a separating agent used for separating the blood into serum components 2 and clot components 3. Reference numeral 7 is a laser beam output means for illuminating the separated blood 1, and 8 is a photo detecting means for receiving the laser beam.

The laser beam is emitted to the separated blood 1 in FIG. 8 so as to scan the blood vertically, and the photo detecting means 8 receives the light passing through the serum components 2. By detecting the amount of change in quantity of light obtained, an upper boundary position 5 and a lower boundary position 6 of the serum components 2 are detected.

In this conventional method, however, since the position to be detected is only in a spot region illuminated by the laser beam, if upper and lower liquid levels of the serum components 2 are oblique or uneven due to viscosity of the serum components or the separating agent, an accurate position of the entire liquid level cannot be detected. There is another problem involved that anticipating such a case where a necessary amount of serum components 2 for analysis cannot be extracted, it is necessary to extract an extra specific amount of serum components when actually extracting serum components.

The present invention devised to solve the above problems has a primary object of providing a specimen testing apparatus capable of accurately measuring the amount of serum components 2 in FIG. 8 even if the upper and lower liquid levels of the serum components 2 vary, without failing to measure a necessary amount of the serum components all the time.

DISCLOSURE OF THE INVENTION

In order to achieve the above object, the invention provides a specimen testing method for taking an image of a container containing blood separated into serum components and clot components by a visual sensor, detecting an upper boundary position of the serum components and a lower boundary position of the serum components from image data output from the visual sensor, and determining the amount of the serum components from the distance between upper boundary position and lower boundary position and the diameter of the container. The specimen testing apparatus of the invention comprises a visual sensor for taking an image of blood separated into serum components and clot components, an image memory for storing digital image data output from the visual sensor, serum component upper boundary position detecting means for detecting an upper boundary position of the serum components from the digital image data stored in the image memory, a serum component lower boundary position detecting means for detecting a lower boundary position of the serum components, and serum component amount measuring means for measuring the amount of the serum components from the upper boundary position and lower boundary position.

The specimen testing method further comprises the steps of taking an image of blood separated into serum components and clot components by a color visual sensor, extracting only the serum components by color information from image data output from the color visual sensor, detecting an upper boundary position of the serum components and a lower boundary position of the serum components, and determining the amount of the serum components from the distance between the upper boundary position and lower boundary position and the diameter of a test tube. The specimen testing apparatus of the invention further comprises a color visual sensor for taking the image of blood separated into serum components and clot components, color extracting means for extracting digital image data composed of specific color components from the digital image data output from the color visual sensor, an image memory for storing the digital image data obtained from the color extracting means, serum component upper boundary position detecting means for detecting an upper boundary position of the serum components from the digital image stored in the image memory, serum component lower boundary position detecting means for detecting a lower boundary position of the serum components, and serum component amount measuring means for measuring the amount of serum components from the upper boundary position and lower boundary position.

According to the method of the invention, even if the upper and lower liquid levels of serum components in the blood are oblique or uneven, accurate serum components suited to a patient can be extracted. Moreover, even if the amount of serum components in blood varies depending on the specimens, it is possible to measure an accurate amount of serum components suited to the patient.

BRIEF DESCRIPTION OF THE DRAWINGS

FIG. 8 is a diagram for explaining a conventional blood testing method.

DESCRIPTION OF THE EMBODIMENT

Figure 1:
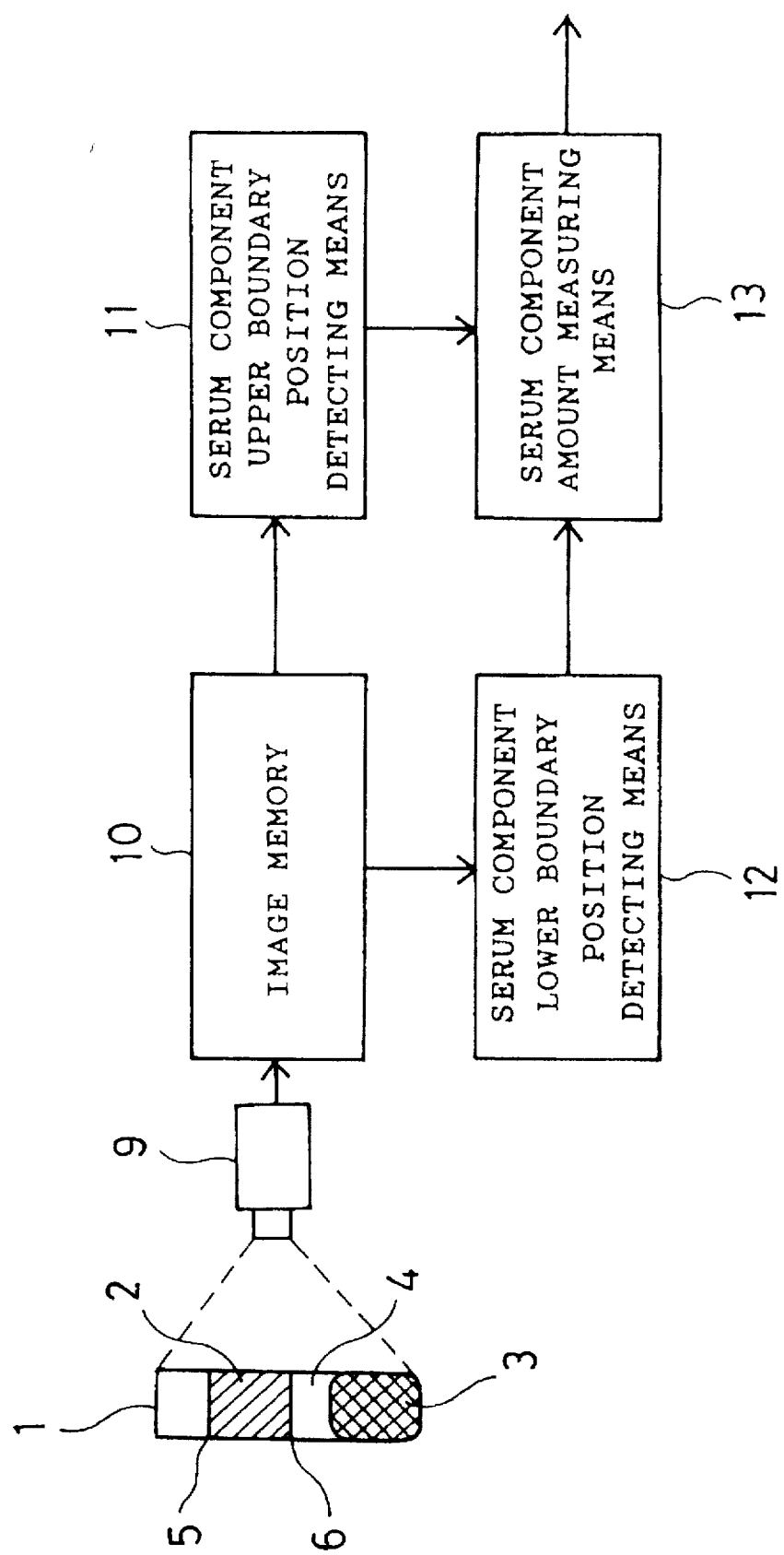
FIG. 1 is a block diagram for explaining a specimen testing apparatus.

Referring now to the drawings, a specimen testing method and its apparatus are described below as an embodiment of the invention.

FIG. 1 shows a specimen testing apparatus of the invention, which is described below. Reference numeral 1 is a separated blood of blood components sampled from a patient and separated by a centrifuge or the like, 2 denotes serum components in the separated blood 1, 3 denotes clot components in the separated blood 1, 4 is a separating agent used for separating the serum components 2 and the clot components 3 in the separated blood 1, 9 is a visual sensor for taking an image of the separated blood 1 and outputting the image as monochromatic digital image data, 10 is an image memory for storing the digital image data output from the visual sensor 9, 11 is a serum component upper boundary position detecting means for measuring an upper boundary position 5 of the serum components 2 from the blood image data stored in the image memory 10, 12 is a serum component lower boundary position detecting means for measuring a lower boundary position 6 of the serum components 2 from the blood image data stored in the image memory 10, and 13 is a serum component amount measuring means for measuring the amount of the serum components from the upper boundary position 5 and lower boundary position 6.

Figure 2:
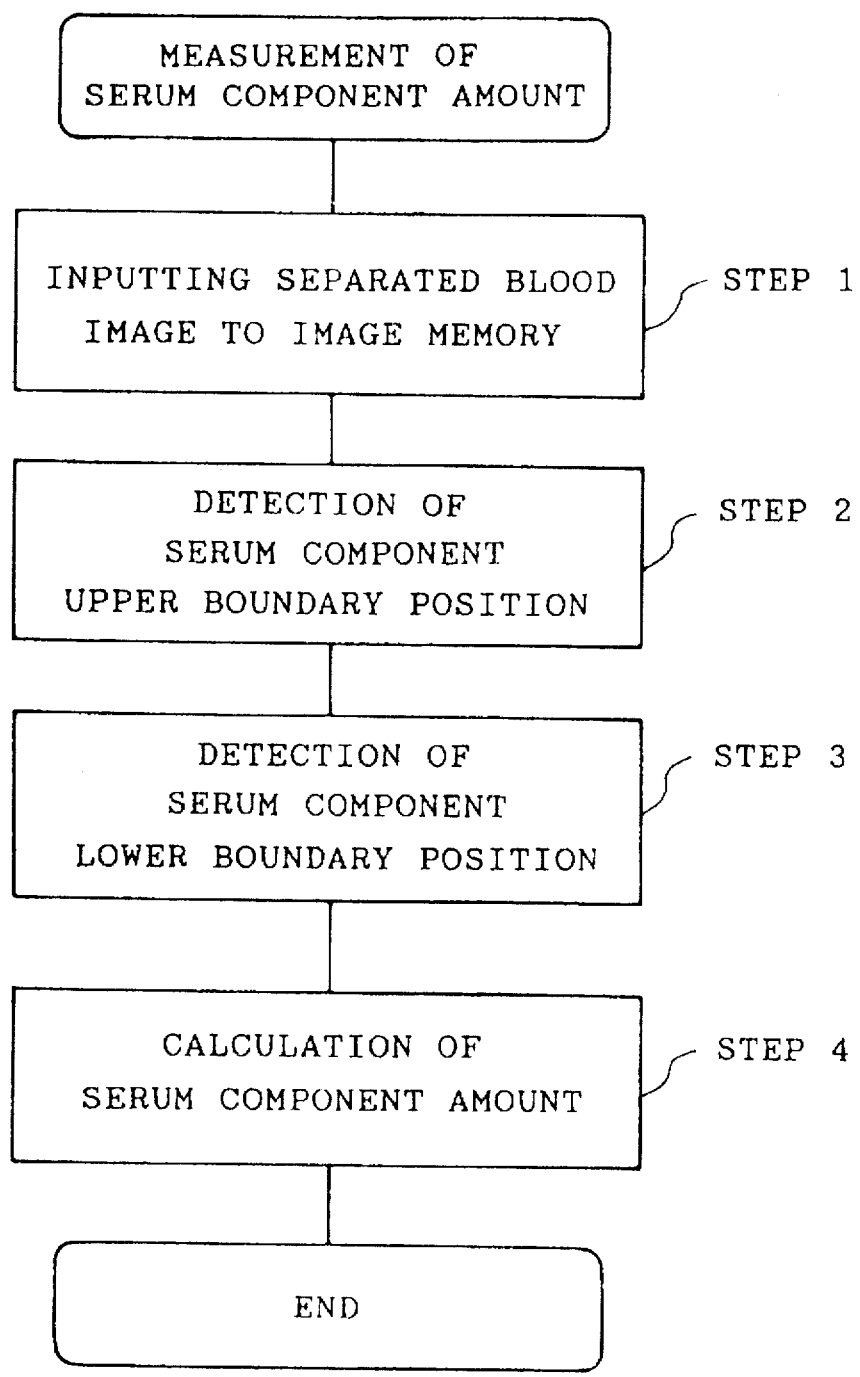
FIG. 2 is an operation flow diagram for explaining the operation of the specimen testing apparatus.

FIG. 2 shows an operation flow of a measuring method of the amount of serum components by the specimen testing apparatus.

According to this operation flow, the principle of the operation of the specimen testing apparatus is described below.

First, at step 1, the image of the separated blood 1 is taken by the visual sensor 9 shown in FIG. 1, and the blood image is taken into the image memory 10.

At next step 2, the serum component upper boundary position detecting means 11 detects the upper boundary position 5 of serum components according to the blood image data taken in the image memory 10.

Figure 3:
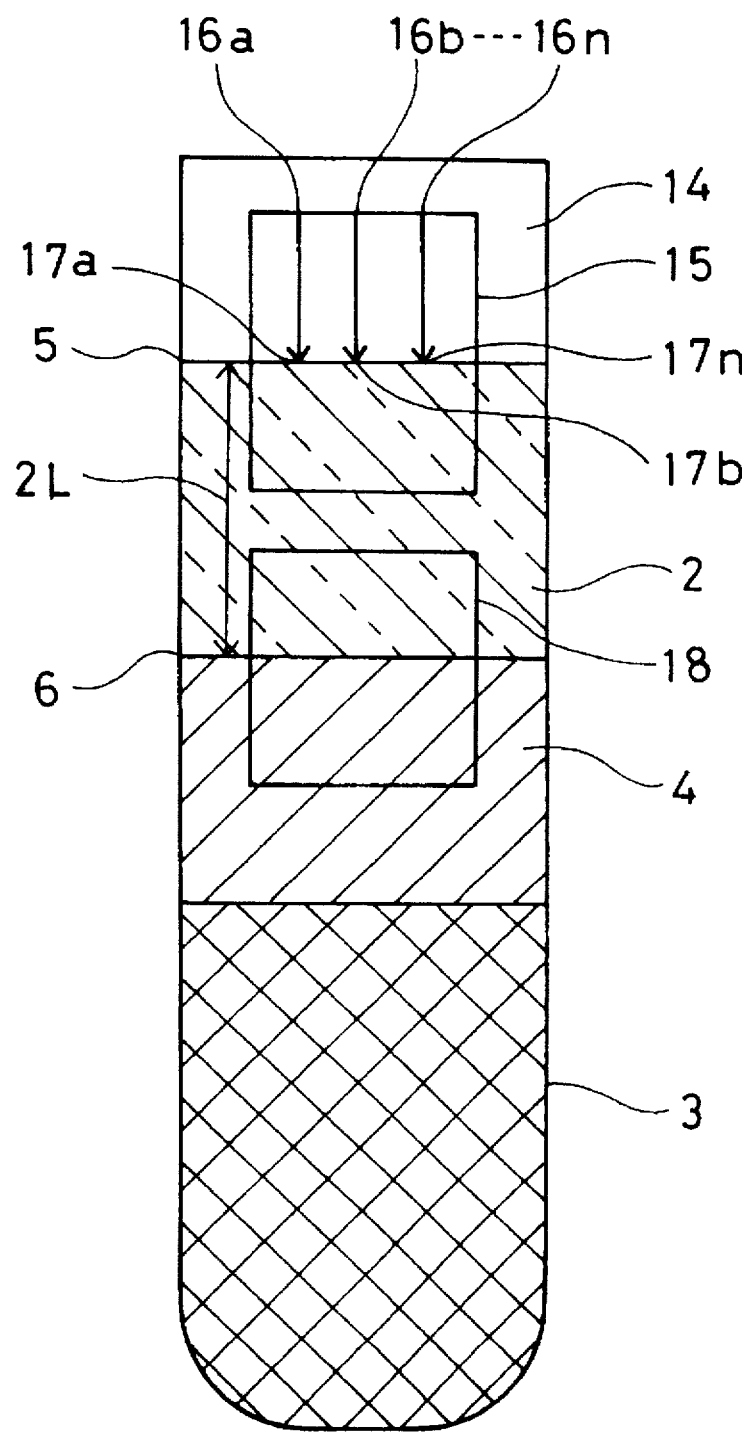
FIG. 3 is a diagram for explaining the operation of measurement of amount of serum components.

FIG. 3 shows a detecting method of the serum component upper boundary position detecting means 11, wherein a plurality of position detecting lines 16a to 16n for detecting the concentration change points are provided in the vertical direction in a predetermined boundary detecting region 15 spreading over the boundary of serum components 2 and space 14 in the image memory 10, and the image data on the position detecting lines 16a to 16n are differentiated linearly, and positions 17a to 17n at peaks of the differential values are detected. As the boundary position 5, an arbitrary position of the detected positions 17a to 17n or a middle position of two arbitrary positions may be used.

As the method of detecting the upper boundary position 5, linear differentiation may be operated on a projection data row obtained by adding image data in every one of all horizontal lines in the boundary detecting region 15, and the positions of peak differential values may be obtained.

Consequently, at step 3, by the serum component lower boundary position detecting means 12, the lower boundary position 6 of serum components is detected from the blood image data taken in the image memory 10. The detecting method of the serum component lower boundary position 6 may be the same as the method shown in step 2 in the predetermined boundary detecting means 18 spreading over the serum components 2 and the separating agent 4 shown in FIG. 3.

At step 4, the amount of serum components is calculated from the serum upper boundary position 5 and the serum lower boundary position 6 obtained at step 2 and step 3, by the serum component amount measuring means 13.

Figure 4:
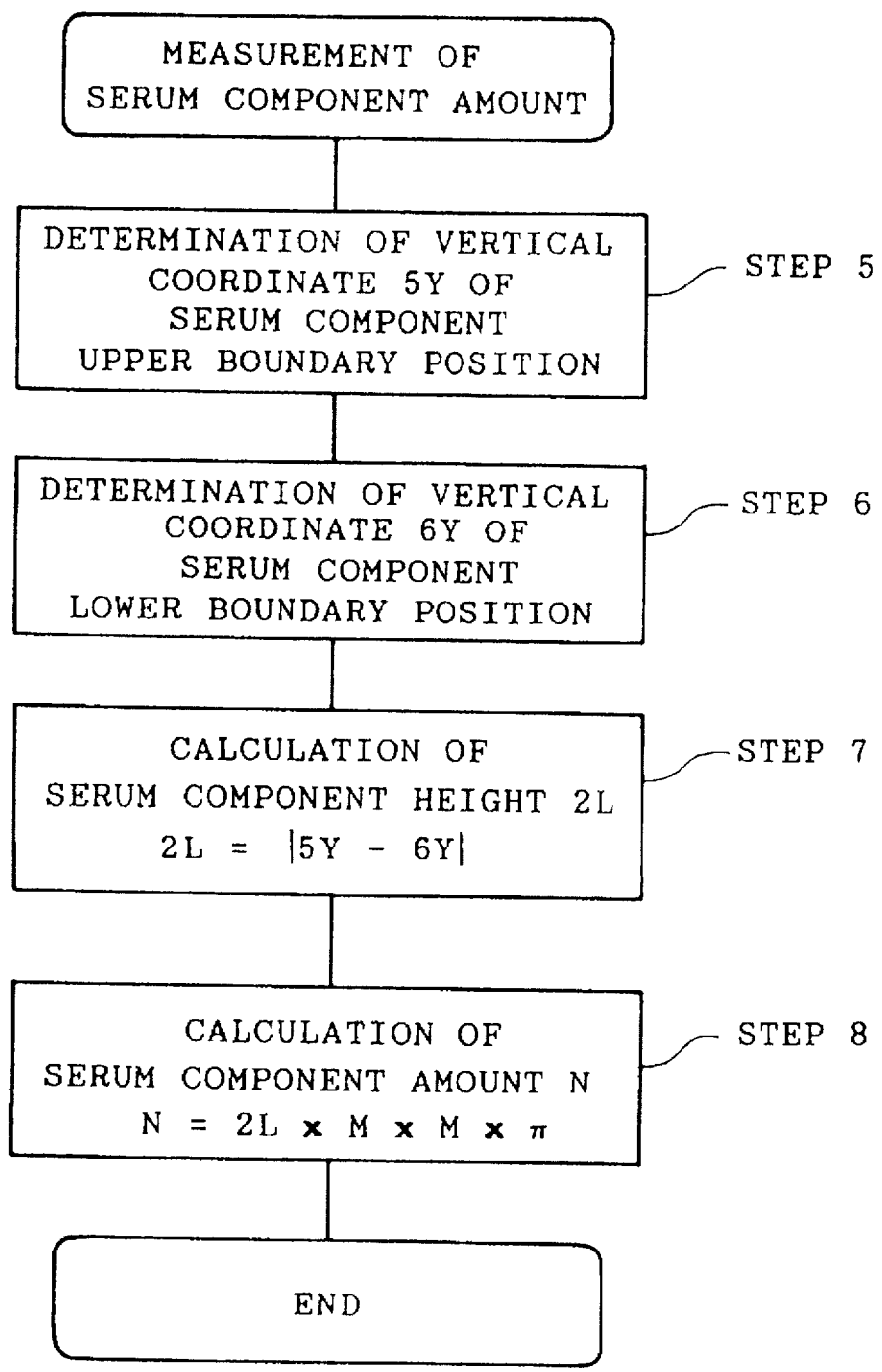
FIG. 4 is an operation flow diagram for explaining the operation of measurement of amount of serum components.

FIG. 4 is a flow showing a calculating method of the amount of serum components, in which a vertical coordinate 5Y of the serum component upper boundary position 5 is determined at step 5. At step 6, a vertical coordinate 6Y of the serum lower boundary position 6 is determined.

At next step 7, an absolute value of the difference between the serum component upper vertical coordinate 5Y and the serum component lower vertical coordinate 6Y is determined, and hence the height 2L of serum components is calculated. At step 8, the serum component amount N is calculated from the diameter M of a test tube containing a predetermined separated blood 1 and the height 2L of serum components calculated at step 5.

Figure 5:
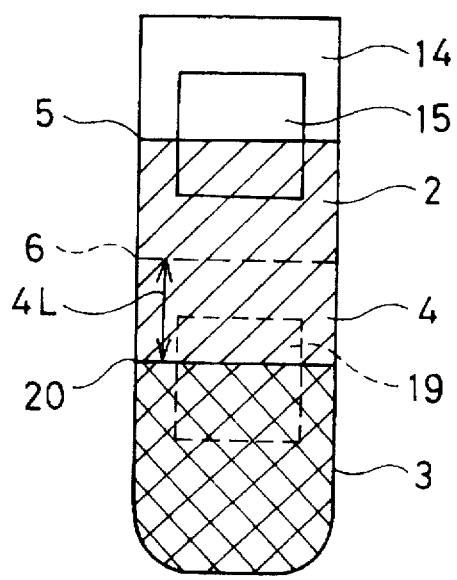
FIG. 5 is a diagram for explaining the operation of measurement of amount of serum components when the boundary between serum components and separating agents cannot be detected.

Further, as shown in FIG. 5, if there is no contrast between the separating agent 4 and the serum components 2 at step 3 in FIG. 2, and the serum component lower boundary position 6 cannot be accurately obtained, provided the amount 4L of the separating agent 4 be a specific amount, the boundary position between the clot components 3 and the separating agent 4 is determined by detecting a clot upper boundary position 20 in a predetermined boundary detecting region 19 same as in step 2 in FIG. 2, and the serum component lower boundary position 6 higher by the portion of the separating agent amount 4L can be calculated.

Figure 6:
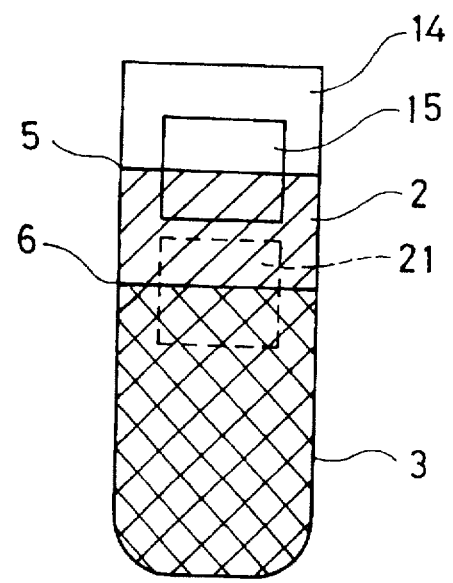
FIG. 6 is a diagram for explaining the operation of measurement of amount of serum components in the absence of separating agents.

Furthermore, in the case of the separated blood 1 in the absence of a separating agent 4 as shown in FIG. 6, same as in step 3 in FIG. 2, the serum lower boundary position 6 can be detected in a predetermined boundary detecting region 21.

From the serum component amount N thus obtained in the method shown in FIG. 2, an accurate amount of serum components 2 can be extracted.

Figure 7:
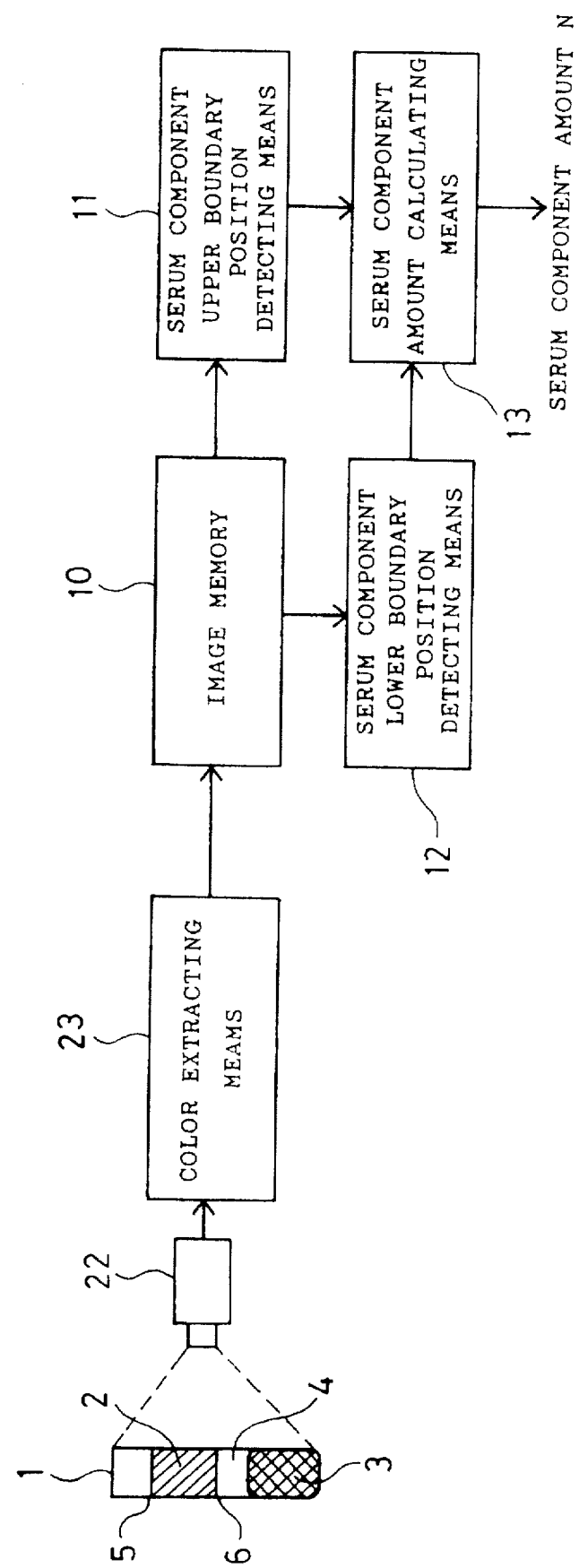
FIG. 7 is a block diagram for explaining a specimen testing apparatus by color extraction.

Still more, FIG. 7 shows a different specimen testing method and apparatus according to the invention. Reference numeral 22 denotes a color visual sensor for taking the image of separated blood 1 and outputting the image as color digital image data consisting of red component data R, green component data G, and blue component data B. Reference numeral 23 is a color extracting means for transforming RGB color image data output from the color visual sensor 22 into three attributes of color, that is, hue information H, luminance information V, and saturation information C, and extracting only the image data included in the range of a preliminarily detected detection serum color from the three attribute data. The image data output from the color extracting means 23 is stored in the image memory 10, and the upper boundary position 5 and the lower boundary position 6 of the serum components 2 are measured by the method shown after step 2 in FIG. 2, and the serum component amount N is measured.

By this method, serum components 2 having arbitrary color components can be extracted, so that the serum components can be analyzed separately.

What is claimed is:

1. A specimen testing method comprising the steps of taking an image of a container containing blood separated into serum components and clot components by a visual sensor, storing an image data output from the visual sensor as a digital image in an image memory, detecting an upper boundary position of the serum components and a lower boundary position of the serum components from the image data stored in the image memory, and determining the amount of the serum components from the distance between the upper boundary position and lower boundary position and the diameter of the container.

2. A specimen testing method according to claim 1, wherein a plurality of position detecting lines for detecting concentration change points are provided in a predetermined boundary detecting region including the upper boundary position and lower boundary position of the serum components, the image data on the position detecting lines is differentiated linearly, positions of peak differential values are detected, an average position is calculated from the detected positions of each peak values, and the upper boundary position and lower boundary position are determined.

3. A specimen testing method comprising the steps of taking an image of blood separated into serum components and clot components by a color visual sensor, transforming color information obtained from color image data output from the color visual sensor into three attributes of color consisting of hue information, luminance information and saturation information, extracting with a color extracting means only color image data included in a range of a predetermined detection serum color from the hue, luminance and saturation information, storing the image data output by the color extracting means in an image memory, detecting an upper boundary position of the serum components and a lower boundary position of the serum components from the image data stored in the image memory, and determining the amount of the serum components from the distance between the upper boundary position and lower boundary position and the diameter of the container.

4. A specimen testing apparatus comprising a visual sensor for taking an image of blood separated into serum components and clot components, an image memory for storing digital image data output from the visual sensor, a serum component upper boundary position detecting means for detecting an upper boundary position of the serum components from the digital image data stored in the image memory, a serum component lower boundary position detecting means for detecting a lower boundary position of the serum components, and a serum component amount measuring means for measuring the amount of the serum components from the upper boundary position and lower boundary position.

5. A specimen testing apparatus according to claim 4, wherein the serum component upper boundary position detecting means and lower boundary position detecting means are capable of determining the upper boundary position and lower boundary position by linearly differentiating image data on a plurality of position detecting lines included in a predetermined boundary detecting region in the image memory, said position detecting lines being provided for detecting concentration change points, detecting peak positions of the differential values, and calculating the average of the detected positions of each peak values.

6. A specimen testing apparatus comprising a color visual sensor for taking images of blood separated into serum components and clot components, a color extracting means for extracting digital image data composed of specific color components from the digital image data output from the color visual sensor, an image memory for storing the digital image data obtained from the color extracting means, a serum component upper boundary position detecting means for detecting an upper boundary position of the serum components from the digital image stored in the image memory, a serum component lower boundary position detecting means for detecting a lower boundary position of the serum components, and a serum component amount measuring means for measuring the amount of serum components from the upper boundary position and lower boundary position.

* * * * *